United States Patent [19]
Reynolds et al.

[11] Patent Number: 5,147,320
[45] Date of Patent: Sep. 15, 1992

[54] CATHETER AFFIXING AND ANCHORING PAD AND METHOD OF USE

[75] Inventors: Valdon G. Reynolds, Bountiful; John A. Davison, Sandy, both of Utah

[73] Assignee: Sorex Medical, Inc., Salt Lake City, Utah

[21] Appl. No.: 695,258

[22] Filed: May 3, 1991

[51] Int. Cl.⁵ .................................................. A61M 5/32
[52] U.S. Cl. ........................................ 604/174; 604/180
[58] Field of Search ............... 604/174, 176, 177, 179, 604/180; 128/DIG. 26

[56] References Cited

U.S. PATENT DOCUMENTS

| | | | |
|---|---|---|---|
| 2,727,512 | 12/1955 | Muller | 604/180 |
| 3,568,679 | 3/1971 | Reif | 128/DIG. 26 X |
| 3,630,195 | 12/1971 | Santomieri | 604/180 |
| 3,973,565 | 8/1976 | Steer | 128/214.4 |
| 4,029,103 | 6/1977 | McConnell | 604/179 |
| 4,082,094 | 4/1978 | Dailey | 128/214 R |
| 4,129,128 | 12/1978 | McFarlane | 128/133 |
| 4,250,880 | 2/1981 | Gordon | 128/214 R |
| 4,316,461 | 2/1982 | Marais et al. | 128/214 R |
| 4,449,975 | 5/1984 | Perry | 604/179 |
| 4,605,397 | 8/1986 | Ligon et al. | 604/179 |
| 4,632,670 | 12/1986 | Mueller, Jr. | 604/174 |
| 4,711,636 | 12/1987 | Bierman | 604/180 |
| 4,981,475 | 1/1991 | Haindl | 128/DIG. 26 X |

*Primary Examiner*—John G. Weiss
*Assistant Examiner*—Jeffrey A. Smith
*Attorney, Agent, or Firm*—Berne S. Broadbent

[57] ABSTRACT

A catheter affixing and anchoring device including a unitary thermoplastic elastomer pad through which a catheter clasping tunnel is bored to lead a catheter to and through a directional channel. The channel affixes the catheter in a preferred configuration preparatory to anchoring of the device and the catheter assembly to the body of a medical patient by means of a simple procedure and in a manner which allows for easy and repeated cleaning of the insertion site with limited disturbance to the catheter assembly or underlying body tissues. This invention is particularly well suited to use in connection with parenteral infusion, drainage of bodily fluid accumulations and administration of medicaments in liquid form directly to various parts of the body. This invention may also advantageously be used in other applications requiring the infusion of fluids, such as, for example, hyperalimentation.

19 Claims, 2 Drawing Sheets

CATHETER AFFIXING AND ANCHORING PAD AND METHOD OF USE

BACKGROUND

1. The Field of the Invention

This invention relates to an improved catheter affixation and anchoring device. More particularly, this invention relates to a novel apparatus for positioning a catheter in a desired configuration and anchoring the catheter assembly to the body of a patient.

2. The Background Art

Heretofore, means for securing catheter assemblies and cannula securing devices have varied widely. Some have been either simplistic in function and effectiveness or excessively invasive. Others have been comprised of multiple components and adapted for use in only a limited number of applications for administration of parenteral fluids. Typically, these latter methods and devices have been time consuming to use, have required multiple components for assembly and varied materials for manufacture of such multiple components, have included relatively complicated structural features, and have been adaptable for use in only a limited number of specific medical procedures.

In common nonproprietary practice, a catheter is affixed to a medical patient by use of an adhesive or surgical tape placed over the catheter atop the skin. Similarly, the hub between the catheter and cannula is also maintained in place by tape. A safety loop is typically formed in the catheter tubing to ensure that any tension applied to the catheter is not passed directly to the cannula, but instead is taken up in the slack of the safety loop. As expected, each of the several times this taping process is to be performed over the course of a given catheterization procedure, a considerable amount of the time of a medical practitioner is consumed. Moreover, this somewhat complicated taping process must be repeated several times in this outmoded approach, such that substantial tape is wasted. Furthermore, the frequent application and removal of typically strong adhesive tape regularly results in the excoriation of the skin underneath the tape and at the site of the cannula insertion. Difficulties attendant to removal and reapplication of tape in this context give practitioners incentives to change the tape less frequently, thereby causing increased incidence and severity of infection and skin suffocation. The ability of practitioners to view the site covered by tape is also diminished in indirect proportion to adequacy of the amount of tape used.

Occasionally the attachment of the catheter is effected or enhanced by an actual suturing of the catheter to the skin of the patient. The difficulties of cleaning, pain, potential scarring, and increased risk of infection inherent in this approach are all readily apparent. In addition, many states currently require a license before this type of suturing procedure can be used.

Several relatively cumbersome proprietary devices have recently proliferated. One system, the Intravenous Vascular Stabilizer of U.S. Pat. No. 4,316,461 issued to Marais et al. on Feb. 23, 1982, describes a device with at least four parts, with the commensurate rise in manufacturing complexity and cost. Two of the parts, which are made of a more pliant material than the other semi-rigid parts, perform the function of anchoring the device with straps around a limb of the patient. A number of clips can be attached to the device to accommodate infusion tubing, Y connectors and the like. The functional application of this device is limited to vascular infusion, as well as elevation and lateral stabilization of the blood vessels which are to be infused.

Another device whose function is limited to circumstances involving intravenous infusion, the Intravenous Anchor and Wound Shield of U.S. Pat. No. 4,449,975 issued to Perry on May 22, 1984, likewise utilizes straps for fastening the device to a limb of the patient. Devices conforming to this disclosure require at least three parts, two of which form the two straps which anchor the semi-rigid device in place. The catheter leads from the cannula and hub through the straps and over the semi-rigid portion of the device. Then the catheter is characteristically bent to double back in a safety loop and interweave through the straps in the opposite direction. While one object of this device is to provide an anchoring system in which the amount of adhesive contact with the skin is substantially reduced, the strapping implements on this apparatus and devices of a similar design may tend to constrict the circulatory flow within the limb to which the apparatus is anchored. Another disadvantage is the potential for lateral migration of the catheter underneath the anchoring straps. Such a migratory shift in the positioning of one length of the catheter can result in patient discomfort as the fastening straps press the catheter into the skin of the patient or, worse, cause a segment of the catheter tube near the apex of the catheter safety loop to collapse and thereby partially or completely restrict the steady flow of parenteral fluids to the body.

The Catheterization System described in U.S. Pat. No. 4,711,636 issued to Bierman on Dec. 8, 1987, is likewise comprised of multiple parts of varied materials with narrow application, addresses the potential for lateral migration by essentially affixing the cannula, needle or other stylet to the device itself. The catheter is replaceably connected to a channel through the device which is in fluid communication with the cannula. The cannula remains in-dwelling within the body of the medical patient. Accordingly the device is intended to be self-adhered to the skin one time only throughout the duration of the catheterization procedure, allowing changing of the catheter tubing only. This approach by design inherently possesses the potential for accumulation of microbial contamination at and near the insertion site. In addition, the device necessarily must utilize a specially designed, customized tubing, preventing its applicability to more universally available and less expensive catheter resources.

BRIEF SUMMARY AND OBJECTS OF THE INVENTION

In view of the foregoing, it is a primary object of the present invention to provide a novel, unitary device for affixing and anchoring a catheter assembly to the body of a medical patient.

It is also an object of the present invention to reduce the cost of manufacturing catheter affixing and anchoring devices by reducing the number of necessary parts and by improving the design and method of production and use.

Additionally, it is an object of the present invention to provide a catheter affixing and anchoring apparatus which is easy to use and which may be used with conventional catheter tubing.

It is a further object of the present invention to provide a catheter affixing and anchoring apparatus which effectively secures the catheter against lateral displacement.

It is a still further object of the present invention to provide a catheter affixing and anchoring apparatus which is adapted for ready use in a wide variety of applications.

Consistent with the foregoing objects, and in accordance with the invention as embodied and broadly described herein, a novel catheter affixing and anchoring device is disclosed in a presently preferred embodiment of the present invention as including a unitary thermoplastic elastomer pad through which a catheter clasping tunnel is bored to lead a catheter to and through a directional channel. The channel affixes the catheter in a preferred configuration preparatory to anchoring of the device and the catheter assembly to the body of a medical patient by means of a simple procedure and in a manner which allows for easy and repeated cleaning of the insertion site with limited disturbance to the catheter assembly or underlying body tissues.

As set out further below, this invention provides, with improved simplicity and reduced cost, a considerably less painful, less invasive, more easily cleaned and more freely breathable apparatus for securing a catheter assembly to the body of a medical patient. This invention is particularly well suited to use in connection with parenteral infusion, drainage of bodily fluid accumulations and administration of medicaments in liquid form directly to various parts of the body. This invention may also advantageously be used in other applications requiring the infusion of fluids, such as, for example, hyperalimentation.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENT

Figure 1:
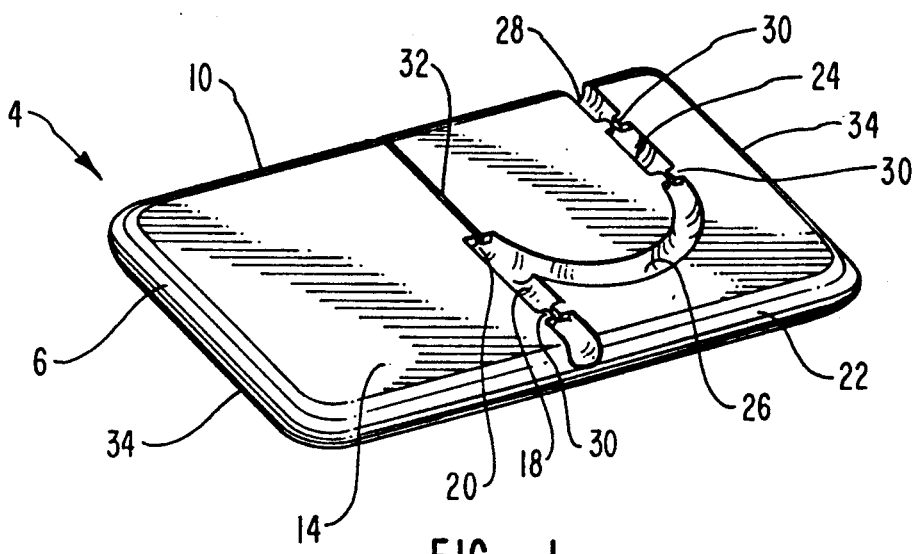
FIG. 1 is a perspective view of one presently preferred embodiment of the catheter affixing and anchoring device of the present invention.

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 5, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

Referring particularly to FIGS. 1 through 4, the catheter affixing and anchoring device, generally designated 4, is illustrated. While the outside edge 6 of the device 4 illustrated is susceptible to being defined in various shapes and contours for stylistic purposes but with little functional benefit, it is illustrated as being defined by a substantially rectangular exterior periphery. The device 4, in its simplest form, is a one piece wafer-like pad ideally with beveled or rounded edges 6 surrounding substantially its entire periphery. The rounded edges 6 tend to mitigate the friction of the edge 6 of the device 4 against the body of a medical patient.

A substantially linear passageway or through-bore 8 extending from the front 10 to substantially the center 12 of the device 4 is located beneath but adjacent to the exposed surface 14 of the device 4. The cross-sectional diameter of the through-bore 8 does not extend at any point between the exposed surface 14 and the closed surface 16 beyond approximately one half of the distance beneath the exposed surface 14.

The through-bore 8 is in open communication with a channel 18 which is substantially completely exposed to the exposed surface 14 along substantially its entire length. The depth of the channel 18 extends from the exposed surface 14 toward the closed surface 16 not beyond approximately two thirds of the distance between the exposed surface 14 and the closed surface 16. The channel 18 is intended to be of a depth sufficient to enable the device 4 to accommodate the placement and retention of a portion of the length of a catheter into the channel 18 such that the portion of the catheter is visible from the exposed surface 14 of the device 4 and lies substantially entirely in cross-sectional diameter below the exposed surface 14.

Figure 2:
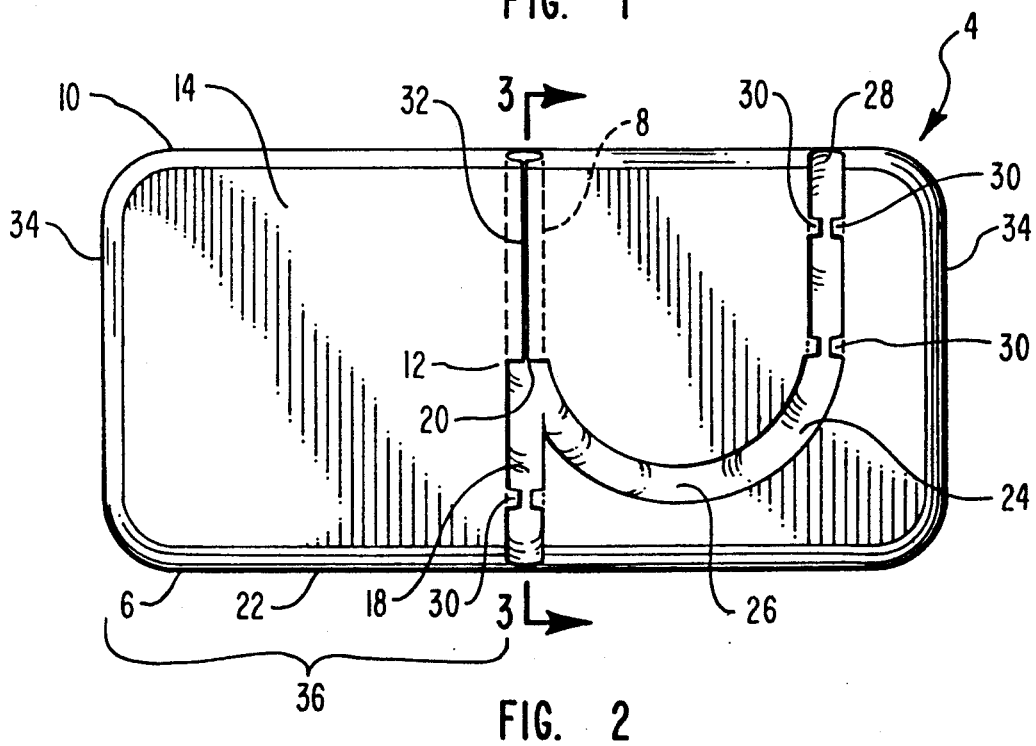
FIG. 2 is a top plan view illustrating one presently preferred embodiment of the catheter affixing and anchoring device of the present invention, the subsurface channels and passageway being depicted with broken lines.
Figure 3:
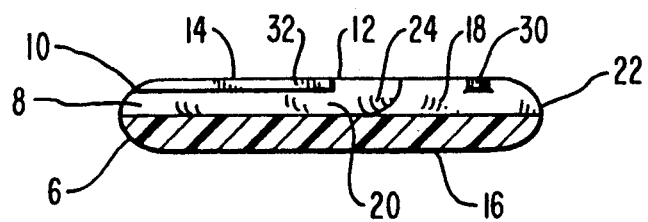
FIG. 3 is a lateral cross-sectional view of the embodiment of FIGS. 1 and 2 taken along lines 3—3 of FIG. 2.

The specific configuration of the channel 18 can vary widely according to the specification of a user. In the illustrated embodiment, the configuration of the channel 18 is depicted in FIGS. 1, 2 and 3 to extend from and in communication with the opening 20 of the through-bore 8 located at approximately the center 12 of the device 4 and exiting to the rear 22 of the device 4.

An alternate channel 24 leading from the same opening 20 of the through-bore 8 and curving in an approximately "U" shaped arc 26 continues away from the opening 20 of the through-bore 8 around the arc 26 and exits to an opening 28 at the front 10 of the device 4. The arc 26 must have a radius of sufficient degree to enable a catheter within the alternate channel 24 to communicate fluids around the arc 26 without a material restriction from excessive bending of such a catheter at any point along the arc 26. Like the principal channel 18, the alternate channel 24 is intended to be of sufficient depth to accommodate and retain a portion of the length of a catheter substantially entirely in cross-sectional diameter below the exterior surface 14. The alternate channel 24 is likewise intended to be substantially completely exposed to the exposed surface 14 along substantially its entire length.

It can be appreciated that channels 18 and 24 of this sort can be multiplied, formed in differing configurations and, where preferred function might dictate, formed to direct catheters to levels deeper within the device 4 or alternatively to direct catheters to shallower levels such that the cross-sectional diameter of such catheters lies at a point partially or entirely above the exposed surface 14 of the device 4 at virtually any point along such channels 18 and 24.

At preferred points along the channels 18 and 24 barbs 30 are located to clasp a portion of the length of a catheter which is placed along the course of a channel 18 or 24. In addition to affixing and securing the catheter in a configuration conforming to the shape of the channel 24, the barbs 30, as illustrated in FIGS. 1, 2 and 3, retain the catheter substantially entirely in cross-sectional diameter in a position below the level of the exterior of the exposed surface 14 to prevent inadvertent hooking or taping of the catheter within the channel 18 or 24 in such a manner as to extract the catheter from the intended position within the channel 18 or 24.

A longitudinal slit 32, illustrated in FIGS. 1, 2 and 3, may be, and in the present embodiment is, interposed along the through-bore 8 between the front 10 of the device 4 and the opening 20 of the through-bore 8. The slit 32 in this embodiment extends from the through-bore 8 longitudinally axially to the exposed surface 14 along the entire length of the through-bore 8. Where this slit 32 feature is utilized, as in the present embodiment, a catheter can be set into the through-bore 8 through the slit 32. In an alternative but probably less desirable embodiment, the catheter could instead be threaded into the through-bore 8.

The catheter setting procedure utilizing the slit 32 is accomplished by bending the sides 34 in the direction of the closed surface 16 while simultaneously pushing the closed surface 16 approximately along the defined line 3—3 in a hinging manner in the general direction of the exposed surface 14 so as to cause the slit 32 to open up to receive and accommodate a portion of the length of a catheter. The device 4 is then released and allowed to return to its biased substantially planar position allowing the slit 32 to close firmly over the catheter and affixing the catheter snugly within the through-bore 8.

Figure 4:
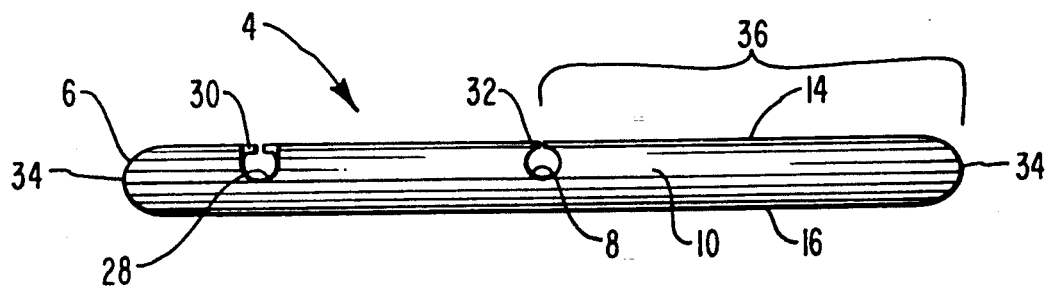
FIG. 4 is a front view of one presently preferred embodiment of the catheter affixing and anchoring device of the present invention.

An unchanneled extended side 36 may be, and as illustrated in FIGS. 2 and 4 is, included in the body of the device 4 to accomplish the function of lending a stabilizing effect to the device 4 when it is anchored to the body of a medical patient.

Figure 5:
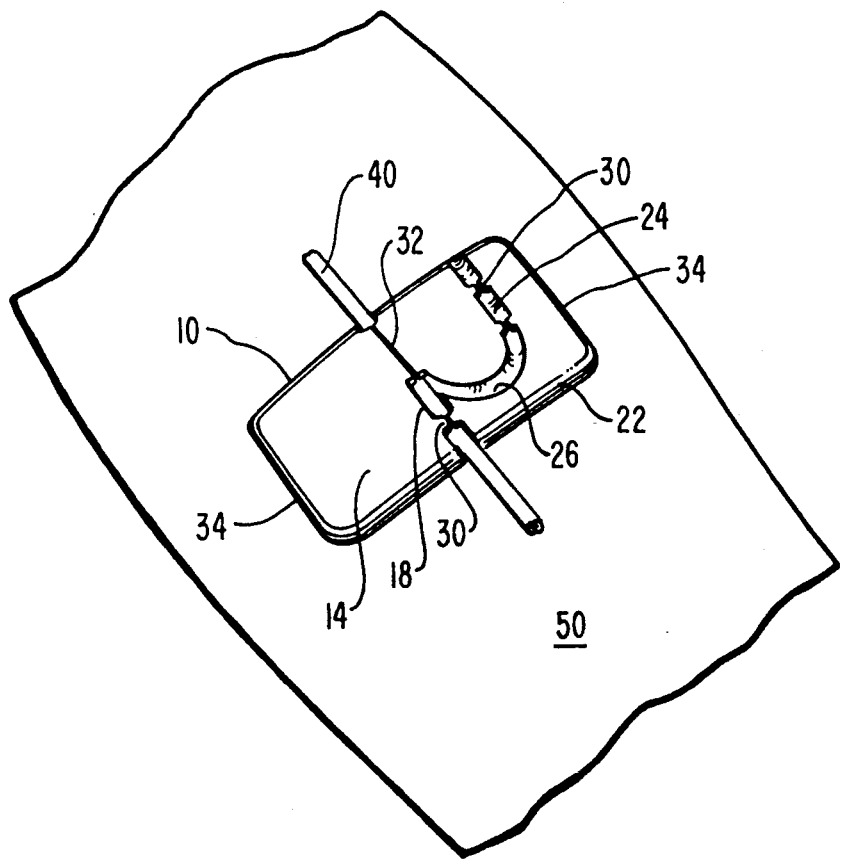
FIG. 5 is a perspective view of one presently preferred embodiment of the catheter affixing and anchoring device of the present invention in use anchoring a catheter to the body of a patient.

Referring now more particularly to FIG. 5, the device 4 and a catheter 40 may be anchored by any of a number of means to the body 50 of a medical patient. Alternatives include use of a self-adhesive surface on the closed surface 16 of the device 4 to adhere the closed surface 16 of the device 4 and catheter assembly to the body 50 of a medical patient. Alternatively, the device 4 and catheter assembly 40 can be anchored by placing them with either the exposed surface 14 or the closed surface 16 against the body 50 of the medical patient and then placing any of a variety of suitable adhesive patches over them. Examples of products of suitable adhesion strength currently marketed include OPSITE ™ of T. J. Smith and Nephew Limited, and COBA ® and Tegader ™ both of 3M Corporation. Conventional bandages, though potentially of too great an adhesive strength, may also be utilized.

Variations from the specific embodiment described above are, of course, possible. It is observed that the channels 18 and 24 could be alternatively configured. Also, it will be readily appreciated that members 30 defining the barbs which clasp the catheter could be located in greater numbers or with somewhat modified shape and spacing along the channels. Similarly, additional features could be included to enhance in a creative, albeit somewhat complicated and more expensive fashion, the more functionally superficial capabilities of the device as, for instance, where various implements are imbedded in the body of the device to provide further catheter clasping means or where fenestrations through the body of the device 4 are provided to facilitate air circulation and provide means for attaching sutures through the device 4.

The components can, of course, be formed of a wide variety of suitable materials. Manufacture could conceivably be complicated with use of multiple materials or could remain limited to a single plastic material, preferably one which is dimensionaly stable when exposed to liquids and when exposed to temperatures below approximately 150 degrees Fahrenheit. The body of the device 4, for example, could be formed of silicone, rubber, or any other suitable thermoplastic elastomer or resilient, semi-pliable material.

From the above discussion, it will be appreciated that the present invention provides an improved structure and design for affixing a catheter in a particular configuration and anchoring the catheter assembly. Moreover, since the device of the present invention has as few as one part, assembly is unnecessary and the cost of the manufacturing process is negligible.

The present invention further provides a catheter affixing and anchoring apparatus which is easy to use and which may be used with conventional catheter tubing. By retaining the catheter tubing in an open channel, the apparatus of the present invention which effectively secures the catheter against lateral displacement. The apparatus is also very versatile and is adapted for ready use in a wide variety of applications.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description All changes which come within the meaning and range of equivalency of the claims are to be embraced within their scope.

What is claimed and desired to be secured by United States Letters Patent is:

1. An apparatus for affixing and anchoring a catheter to the body of a patient, the apparatus comprising:

a pad having a first surface, a second surface and a peripheral edge;

a passageway extending from said peripheral edge of the pad, through a portion of the pad between said first and second surfaces and terminating in an opening located within the pad and away from the peripheral edge thereof, the size and configuration of the passageway being such that the passageway can snugly receive a portion of said catheter therein;

an open channel formed in the first surface of the pad and communicating with the passageway through said opening, said open channel extending from said opening to the peripheral edge of the pad, the size and configuration of the channel being such that the channel can receive therein a portion of the catheter extending from the opening formed by the passageway; and wherein the passageway and the open channel are configured and positioned so as to permit substantially unrestricted fluid flow through said catheter when portions of said catheter are received therein.

2. An apparatus for affixing and anchoring a catheter to the body of a patient as defined in claim 1 wherein the first and second surfaces of the pad are substantially planar surfaces which are substantially parallel to one another.

3. An apparatus for affixing and anchoring a catheter to the body of a patient as defined in claim 1 wherein the depth of the open channel is such that said portion of the catheter received in the channel lies substantially entirely within the pad between said first and second surfaces thereof.

4. An apparatus for affixing and anchoring a catheter to the body of a patient, the apparatus comprising:

a pad having a substantially planar first surface, a substantially planar second surface and a peripheral edge, said first and second surfaces of the pad being substantially the same size and shape and lying substantially parallel to one another;

a passageway extending from said peripheral edge of the pad, through a portion of the pad between said first and second surfaces and terminating in an opening located within the pad and away from the peripheral edge thereof, the size and the configuration of the passageway being such that the passageway can snugly receive a portion of said catheter therein;

at least one open channel formed in the first surface of the pad and communicating with the passageway through said opening, said open channel extending from said opening to the peripheral edge of the pad, the size and configuration of the channel being such that the channel can receive therein a portion of the catheter extending from the opening formed by the passageway, the depth of the open channel being such that said portion of the catheter received in the channel lies substantially entirely within the pad between said first and second surfaces thereof; and wherein the passageway and the open channel are configured and positioned so as to permit substantially unrestricted fluid flow through said catheter when portions of said catheter are received therein.

5. An apparatus for affixing and anchoring a catheter to the body of a patient as defined in claim 4 wherein the pad is substantially rectangular in shape.

6. An apparatus for affixing and anchoring a catheter to the body of a patient as defined in claim wherein peripheral edge of the pad has a substantially rounded shape.

7. An apparatus for affixing and anchoring a catheter to the body of a patient as defined in claim 4 wherein the open channel has a substantially linear configuration.

8. An apparatus for affixing and anchoring a catheter to the body of a patient as defined in claim 7 further comprising a second open channel formed in the first surface of the pad and communicating with the passageway through said opening, the size and configuration of the second channel being such that the channel can receive therein a portion of the catheter extending from the opening formed by the passageway, and the second open channel extending from said opening to the peripheral edge of the pad and having a substantially U-shaped configuration.

9. An apparatus for affixing and anchoring a catheter to the body of a patient as defined in claim 4 further comprising means for retaining a portion of the catheter within the open channel in the pad.

10. An apparatus for affixing and anchoring a catheter to the body of a patient as defined in claim 9 wherein the catheter retaining means comprises resilient barbs extending from the first surface of the pad and into said open channel.

11. An apparatus for affixing and anchoring a catheter to the body of a patient as defined in claim 4 wherein the passageway through the pad lies substantially entirely between the first surface of the pad and points within the pad which are midway between said first and second surfaces thereof.

12. An apparatus for affixing and anchoring a catheter to the body of a patient as defined in claim 4 wherein the peripheral edge of the pad comprises a front edge and a rear edge and wherein the passageway extends from the front edge of the pad and the terminating opening lies substantially midway between the front and rear edges of the pad.

13. An apparatus for affixing and anchoring a catheter to the body of a patient as defined in claim 4 wherein at least a portion of the pad including the passageway and the open channel is formed of a resilient material.

14. An apparatus for affixing and anchoring a catheter to the body of a patient as defined in claim 4 wherein the passageway through the pad is substantially linear.

15. An apparatus for affixing and anchoring a catheter to the body of a patient as defined in claim 4 wherein the first surface of the pad has a slit therethrough which communicates with the passageway along substantially the entire length of the passageway.

16. An apparatus for affixing and anchoring a catheter to the body of a patient as defined in claim 4 wherein the open channel has a depth which is less than approximately two-thirds of the perpendicular distance between the first and second surfaces of the pad.

17. An apparatus for affixing and anchoring a catheter to the body of a patient as defined in claim 4 wherein the open channel has a substantially U-shaped configuration.

18. An apparatus for affixing and anchoring a catheter to the body of a patient as defined in claim 4 wherein the pad includes a stabilizing portion comprising approximately one-third of the pad which is substantially free of passageways and channels.

19. A method for affixing and anchoring a catheter to the body of a patient, the method comprising the steps of:

inserting a portion of the catheter through a passageway which extends from a peripheral edge of a pad through a portion of the pad and terminates in an opening located within the pad and away from the peripheral edge thereof, the size and configuration of the passageway being such that the passageway snugly receives said portion of the catheter therein;

placing a portion of the catheter extending from the opening formed by said passageway in an open channel formed in a first surface of the pad and communicating with the passageway through said opening, said open channel extending from said opening to the peripheral edge of the pad, wherein the passageway and the open channel are configured and positioned so as to permit substantially unrestricted fluid flow through said catheter when portions of said catheter are received therein, and the depth of the open channel being such that said portion of the catheter received in the channel lies substantially entirely within the pad; and affixing the pad to the body of said patient by means other than securing straps.

* * * * *